US011369528B2

(12) United States Patent
Takeda et al.

(10) Patent No.: US 11,369,528 B2
(45) Date of Patent: Jun. 28, 2022

(54) STRETCHABLE LAMINATE AND ARTICLE COMPRISING SAME

(71) Applicant: NITTO DENKO CORPORATION, Osaka (JP)

(72) Inventors: Kohei Takeda, Ibaraki (JP); Shinsuke Ikishima, Ibaraki (JP); Ryuji Kuwabara, Ibaraki (JP)

(73) Assignee: NITTO DENKO CORPORATION, Osaka (JP)

(*) Notice: Subject to any disclaimer, the term of this patent is extended or adjusted under 35 U.S.C. 154(b) by 548 days.

(21) Appl. No.: 16/078,900

(22) PCT Filed: Mar. 3, 2017

(86) PCT No.: PCT/JP2017/008444
§ 371 (c)(1),
(2) Date: Aug. 22, 2018

(87) PCT Pub. No.: WO2017/159398
PCT Pub. Date: Sep. 21, 2017

(65) Prior Publication Data
US 2019/0053959 A1 Feb. 21, 2019

(30) Foreign Application Priority Data

Mar. 15, 2016 (JP) .............................. JP2016-051242

(51) Int. Cl.
*A61F 13/514* (2006.01)
*B32B 25/08* (2006.01)
(Continued)

(52) U.S. Cl.
CPC ........ *A61F 13/51478* (2013.01); *A61F 13/49* (2013.01); *A61F 13/4902* (2013.01);
(Continued)

(58) Field of Classification Search
CPC .......... A61F 13/15731; A61F 13/51464; A61F 13/51466; A61F 13/51476;
(Continued)

(56) References Cited

U.S. PATENT DOCUMENTS 3,265,765 A * 8/1966 Holden ............... C08F 297/046
525/271
5,422,172 A 6/1995 Wu
(Continued)

FOREIGN PATENT DOCUMENTS

| CN | 1128967 A | 8/1996 |
| CN | 101925459 | 12/2010 |

(Continued)

OTHER PUBLICATIONS

Extended European Search Report, European patent Office, Application No. 17766401.8, dated Aug. 14, 2019.
(Continued)

*Primary Examiner* — Catharine L Anderson
*Assistant Examiner* — Lynne Anderson
(74) *Attorney, Agent, or Firm* — Greenblum & Bernstein, P.L.C.

(57) ABSTRACT

Provided is a stretchable laminate that achieves both a weight reduction and an extension strength, and that can be stably produced. Also provided is an article including such stretchable laminate. The stretchable laminate of the present invention includes: an elastomer layer; and an olefin-based resin layer arranged on at least one side of the elastomer layer, wherein when a longitudinal direction of the stretchable laminate is defined as an MD direction and a direction perpendicular to the longitudinal direction is defined as a CD direction, a ratio [10% extension strength in MD direction (N/30 mm)]/[basis weight (gsm)] of the stretchable laminate is 0.14 (N/30 mm·gsm) or more.

25 Claims, 4 Drawing Sheets

(51) Int. Cl.
    *B32B 27/32* (2006.01)
    *A61F 13/49* (2006.01)
    *A61F 13/539* (2006.01)

(52) U.S. Cl.
    CPC .............. *B32B 25/08* (2013.01); *B32B 27/32* (2013.01); *A61F 13/539* (2013.01); *A61F 2013/49023* (2013.01); *B32B 2262/0207* (2013.01)

(58) Field of Classification Search
    CPC ...... A61F 13/51478; A61F 2013/15292; A61F 2013/153; A61F 2013/15325; A61F 2013/51409; A61F 2013/51429; A61F 2013/51431; A61F 2013/51454; B32B 25/08; B32B 27/32
    See application file for complete search history.

(56) References Cited

U.S. PATENT DOCUMENTS

| | | | |
|---|---|---|---|
| 5,592,690 A | 1/1997 | Wu | |
| 5,634,216 A | 6/1997 | Wu | |
| 5,861,074 A | 1/1999 | Wu | |
| 6,472,084 B1 | 10/2002 | Middlesworth | |
| 8,168,853 B2 | 5/2012 | Autran et al. | |
| 8,445,744 B2 | 5/2013 | Autran et al. | |
| 8,664,128 B2 | 3/2014 | Cree | |
| 9,169,384 B2 | 10/2015 | Autran et al. | |
| 9,327,477 B2 | 5/2016 | Autran et al. | |
| 9,469,091 B2 | 10/2016 | Henke et al. | |
| 9,669,606 B2 | 6/2017 | Autran et al. | |
| 9,895,275 B2 | 2/2018 | Autran et al. | |
| 10,500,107 B2 | 12/2019 | Autran et al. | |
| 2007/0141352 A1 | 6/2007 | Calhoun et al. | |
| 2007/0254176 A1 | 11/2007 | Patel et al. | |
| 2009/0191779 A1 | 7/2009 | Cree | |
| 2009/0258210 A1 | 10/2009 | Autran et al. | |
| 2009/0264844 A1 | 10/2009 | Autran et al. | |
| 2010/0040826 A1 | 2/2010 | Autran et al. | |
| 2011/0177735 A1 | 7/2011 | Tasi et al. | |
| 2011/0198116 A1 | 8/2011 | Watari et al. | |
| 2012/0184169 A1 | 7/2012 | Autran et al. | |
| 2013/0237938 A1 | 9/2013 | Autran et al. | |
| 2014/0041786 A1 | 2/2014 | Henke et al. | |
| 2014/0242360 A1 | 8/2014 | Autran et al. | |
| 2014/0330236 A1 | 11/2014 | Schonbeck et al. | |
| 2016/0015576 A1 | 1/2016 | Autran et al. | |

FOREIGN PATENT DOCUMENTS

| | | |
|---|---|---|
| CN | 102189716 | 9/2011 |
| JP | H07-148240 A | 6/1995 |
| JP | H08-217667 A | 8/1996 |
| JP | 3285359 B | 3/2002 |
| JP | 2003-192580 A | 7/2003 |
| JP | 2003-311884 | 11/2003 |
| JP | 2009-519844 A | 5/2009 |
| JP | 2011-083970 | 4/2011 |
| JP | 2011-514178 A | 5/2011 |
| JP | 2011-514391 A | 5/2011 |
| JP | 2013-78928 A | 5/2013 |
| JP | 2015-529581 A | 10/2015 |
| JP | 2016-007754 A | 1/2016 |
| WO | 2007/133128 A1 | 11/2007 |

OTHER PUBLICATIONS

Third Party Observation dated Aug. 4, 2020, obtained on Aug. 11, 2020, in Japanese patent application No. 2016-051242, English translation.

Chinese Office Action dated Oct. 22, 2019, issued in corresponding Chinese patent application No. 201780017297.4 with English translation thereof.

International Search Report issued with respect to Patent Application No. PCT/JP2017/008444, dated May 16, 2017, along with an English translation thereof.

International Preliminary Report on Patentability issued with respect to Patent Application No. PCT/JP2017/008444, dated Sep. 18, 2018, along with an English translation thereof.

Chinese Office Action, Chinese Patent Office, Application No. 201780017297.4, dated Nov. 23, 2020, English translation.

European Notice enclosing Notice of Opposition received in EP Application No. 17766401.8, dated Feb. 23, 2022.

* cited by examiner

STRETCHABLE LAMINATE AND ARTICLE COMPRISING SAME

TECHNICAL FIELD

The present invention relates to a stretchable laminate and an article including the stretchable laminate.

BACKGROUND ART

Various stretchable laminates are adopted in an article such as a sanitary article, for example, a diaper or a mask.

As such stretchable laminate, a stretchable laminate including an elastomer layer and an elastomeric resin layer arranged on at least one side of the elastomer layer has been proposed (for example, Patent Literature 1).

A stretchable laminate to be adopted in an article such as a sanitary article is required to be reduced in weight. However, when an attempt is made to reduce the weight of the stretchable laminate through, for example, a reduction in thickness thereof, there occurs a problem in that its extension strength reduces. In addition, when the reduction in extension strength has occurred at the time of the production of a stretchable laminate having an elongate shape, there occurs a problem in that the stretchable laminate is completely extended in its longitudinal direction at the time of its feeding from a roll, and hence cannot be stably produced.

CITATION LIST

Patent Literature

[PTL 1] US 2011/0177735 A1

SUMMARY OF INVENTION

Technical Problem

The present invention has been made to solve the conventional problems, and an object of the present invention is to provide a stretchable laminate that achieves both a weight reduction and an extension strength, and that can be stably produced. Another object of the present invention is to provide an article including such stretchable laminate.

Solution to Problem

A stretchable laminate according to one embodiment of the present invention is a stretchable laminate having an elongate shape, the stretchable laminate including: an elastomer layer; and an olefin-based resin layer arranged on at least one side of the elastomer layer, wherein when a longitudinal direction of the stretchable laminate is defined as an MD direction and a direction perpendicular to the longitudinal direction is defined as a CD direction, a ratio [10% extension strength in MD direction (N/30 mm)]/[basis weight (gsm)] of the stretchable laminate is 0.14 (N/30 mm·gsm) or more.

In one embodiment, the ratio [10% extension strength in MD direction (N/30 mm)]/[basis weight (gsm)] is 0.15 (N/30 mm·gsm) or more.

In one embodiment, when the stretchable laminate is bonded and fixed onto a glass plate in a state of being extended by 100%, and 0.5 mL of a baby oil (manufactured by Pigeon Corporation, Baby Oil, main component: caprylic/capric triglyceride) is dropped onto a surface of the stretchable laminate, the stretchable laminate is free of a hole 60 minutes after the dropping.

In one embodiment, the olefin-based resin layer is arranged on each of both sides of the elastomer layer.

In one embodiment, the olefin-based resin layer contains a non-elastomeric olefin-based resin.

In one embodiment, a content of the non-elastomeric olefin-based resin in the olefin-based resin layer is from 95 wt % to 100 wt %.

In one embodiment, the non-elastomeric olefin-based resin contains high-density polyethylene.

In one embodiment, the non-elastomeric olefin-based resin contains an α-olefin homopolymer.

In one embodiment, the α-olefin homopolymer includes at least one kind selected from polyethylene and homopolypropylene.

In one embodiment, the polyethylene includes high-density polyethylene.

In one embodiment, the elastomer layer contains an olefin-based elastomer.

In one embodiment, the olefin-based elastomer includes an α-olefin-based elastomer.

In one embodiment, the α-olefin-based elastomer includes at least one kind selected from an ethylene-based elastomer and a propylene-based elastomer.

In one embodiment, the stretchable laminate according to the embodiment of the present invention has stretched portions and non-stretched portions arranged along the CD direction.

In one embodiment, the stretchable laminate has stretched portions and non-stretched portions alternately arranged along the CD direction.

In one embodiment, an area ratio (stretched portions:non-stretched portions) between the stretched portions and the non-stretched portions is from 1:0.5 to 1:3.

In one embodiment, the area ratio (stretched portions:non-stretched portions) is from 1:0.5 to 1:1.2.

In one embodiment, the stretched portions and the non-stretched portions are formed by roll stretching in which two uneven rolls each having recessed portions and protruded portions different from each other in diameter are engaged with each other with the recessed portions and the protruded portions thereof.

In one embodiment, a pitch width of each of the recessed portions is larger than a pitch width of each of the protruded portions.

In one embodiment, a pitch width of each of the recessed portions is from 0.5 mm to 5 mm, and a pitch width of each of the protruded portions is from 0.1 mm to 3 mm.

In one embodiment, the stretchable laminate according to the embodiment of the present invention is subjected to pre-stretching.

In one embodiment, the pre-stretching includes partial stretching.

In one embodiment, a stretching ratio of the partial stretching is 50% or more and less than 100%.

In one embodiment, the stretching ratio is 100% or more and less than 900%.

In one embodiment, the stretchable laminate according to the embodiment of the present invention is used in a sanitary article.

An article according to one embodiment of the present invention includes the stretchable laminate according to the embodiment of the present invention.

Advantageous Effects of Invention

According to the present invention, the stretchable laminate that achieves both a weight reduction and an extension strength, and that can be stably produced can be provided. The article including such stretchable laminate can also be provided.

DESCRIPTION OF EMBODIMENTS

<<<<Stretchable Laminate>>>>

A stretchable laminate of the present invention includes: an elastomer layer; and an olefin-based resin layer arranged on at least one side of the elastomer layer. That is, in the stretchable laminate of the present invention, the olefin-based resin layer may be arranged only on one side of the elastomer layer, or the olefin-based resin layer may be arranged on each of both sides of the elastomer layer. When the stretchable laminate of the present invention has such construction, the stretchable laminate of the present invention can be excellent in oil resistance. In addition, when layers each formed of a resin having an elastomeric property (e.g., an olefin-based elastomer or a styrene-based elastomer) are laminated, blocking is liable to occur between the layers. Accordingly, for example, when the stretchable laminate is turned into a rolled body under a state in which the layers each formed of a resin having an elastomeric property are laminated, blocking easily occurs between the layers each formed of a resin having an elastomeric property, and hence it is liable to be difficult to rewind the stretchable laminate. The stretchable laminate of the present invention can be excellent in blocking resistance because the stretchable laminate includes the olefin-based resin layer on at least one side of the elastomer layer.

The stretchable laminate of the present invention is a stretchable laminate having an elongate shape. In the stretchable laminate of the present invention, its longitudinal direction is defined as an MD direction, and a direction perpendicular to the longitudinal direction is defined as a CD direction.

The stretchable laminate of the present invention may include any appropriate other layer to the extent that the effects of the present invention are not impaired. The number of such any appropriate other layers may be only one, or may be two or more.

In the stretchable laminate of the present invention, it is preferred that the olefin-based resin layer be directly laminated on the elastomer layer. That is, one preferred embodiment of the stretchable laminate of the present invention is an embodiment in which the olefin-based resin layer is directly laminated on at least one side of the elastomer layer. When the olefin-based resin layer is directly laminated on the elastomer layer as described above, the stretchable laminate of the present invention can be more excellent in oil resistance, and can also be more excellent in blocking resistance.

Figure 1:
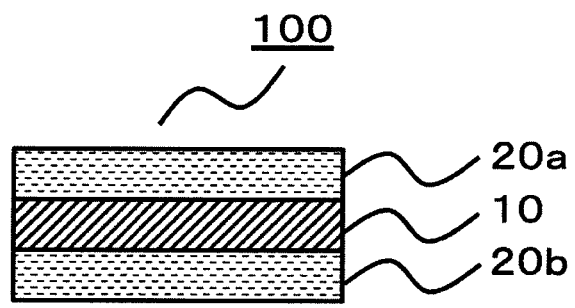
FIG. 1 is a schematic cross-sectional view of a stretchable laminate according to one embodiment of the present invention.

FIG. 1 is a schematic cross-sectional view of a stretchable laminate according to one embodiment of the present invention. A stretchable laminate 100 illustrated in FIG. 1 includes an elastomer layer 10, an olefin-based resin layer 20a arranged on one side of the elastomer layer 10, and an olefin-based resin layer 20b arranged on the elastomer layer 10 on an opposite side to the olefin-based resin layer 20a. A material for bonding the elastomer layer 10 and the olefin-based resin layer 20a and/or for bonding the elastomer layer 10 and the olefin-based resin layer 20b may be present therebetween. Examples of such material include an adhesive, a pressure-sensitive adhesive, and a hot-melt pressure-sensitive adhesive.

The thickness of the stretchable laminate of the present invention is preferably from 10 µm to 500 µm, more preferably from 10 µm to 250 µm, still more preferably from 10 µm to 200 µm, still further more preferably from 10 µm to 100 µm, particularly preferably from 10 µm to 70 µm, most preferably from 10 µm to 50 µm, though the thickness depends on the thickness of the elastomer layer and the thickness of the olefin-based resin layer. When the thickness of the stretchable laminate of the present invention is set within such range, the stretchable laminate of the present invention can be reduced in weight, and hence can be easily used as a material to be used in an article such as a sanitary article, for example, a diaper or a mask.

In the stretchable laminate of the present invention, the ratio [10% extension strength in MD direction (N/30 mm)]/[basis weight (gsm)] of the stretchable laminate is 0.14 (N/30 mm·gsm) or more, preferably 0.145 (N/30 mm·gsm) or more, more preferably 0.15 (N/30 mm·gsm) or more, still more preferably 0.155 (N/30 mm·gsm) or more, particularly preferably 0.16 (N/30 mm·gsm) or more. An upper limit for the ratio [10% extension strength in MD direction (N/30 mm)]/[basis weight (gsm)] is desirably as large as possible. In reality, however, the upper limit is preferably 2.0 (N/30 mm·gsm) or less. When a value for the ratio [10% extension strength in MD direction (N/30 mm)]/[basis weight (gsm)] falls within the range, the stretchable laminate of the present invention has a high extension strength in the MD direction despite being reduced in weight. Accordingly, the stretchable laminate can achieve both the weight reduction and the extension strength, and can be stably produced.

The basis weight of the stretchable laminate of the present invention is preferably from 5 gsm to 500 gsm, more preferably from 5 gsm to 250 gsm, still more preferably from 5 gsm to 200 gsm, particularly preferably from 5 gsm to 100 gsm, most preferably from 5 gsm to 50 gsm. When the basis weight of the stretchable laminate of the present invention falls within the range, the stretchable laminate of the present invention can be sufficiently reduced in weight.

A related-art stretchable laminate may have low oil resistance. For example, there may occur a problem in that an aliphatic oil, such as a baby oil, makes a hole in the stretchable laminate.

When the stretchable laminate of the present invention is bonded and fixed onto a glass plate in a state of being extended by 1.00%, and 0.5 mL of a baby oil (manufactured by Pigeon Corporation, Baby Oil, main component: caprylic/capric triglyceride) is dropped onto the surface of the stretchable laminate, the stretchable laminate is preferably free of a hole 60 minutes after the dropping. When the stretchable laminate of the present invention has such feature, the stretchable laminate of the present invention is excellent in oil resistance. In the present invention, the phrase "the stretchable laminate is free of a hole" in the test typically means that a visible hole or crack to be formed by the dissolution of the stretchable laminate by the baby oil is not formed. Details about a test method for such oil resistance are described later.

When the stretchable laminate of the present invention is bonded and fixed onto the glass plate in a state of being extended by 100%, and 0.5 mL of the baby oil (manufactured by Pigeon Corporation, Baby Oil, main component: caprylic/capric triglyceride) is dropped onto the surface of the stretchable laminate, the time period for which a state in which the stretchable laminate is free of a hole can be maintained after the dropping is preferably 2 hours, more preferably 5 hours, still more preferably 10 hours, particularly preferably 24 hours. When the time period is such preferred time period as described above, the stretchable laminate of the present invention is more excellent in oil resistance.

The stretchable laminate of the present invention has stretched portions and non-stretched portions arranged along the CD direction, and more preferably has stretched portions and non-stretched portions alternately arranged along the CD direction. When the stretchable laminate of the present invention has such structure, the stretchable laminate of the present invention can achieve both the weight reduction and the extension strength to a larger extent, and can be more stably produced.

Figure 2:
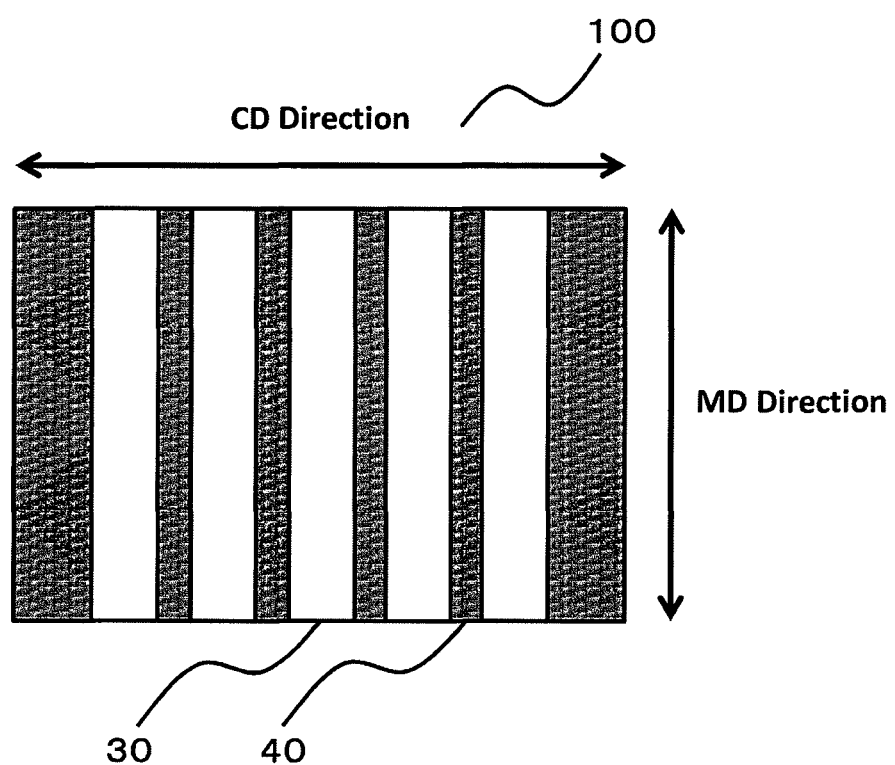
FIG. 2 is a schematic plan view of the stretchable laminate according to one embodiment of the present invention.

FIG. 2 is a schematic plan view of the stretchable laminate according to one embodiment of the present invention when the stretchable laminate of the present invention has stretched portions and non-stretched portions alternately arranged along the CD direction. In FIG. 2, the stretchable laminate 100 has stretched portions 30 and non-stretched portions 40 alternately arranged along the CD direction. When the stretchable laminate of the present invention has such structure, the non-stretched portions continuously remain in the MD direction, and hence non-elasticity remains in the MD direction, and on the other hand, elasticity can be expressed in the CD direction. Thus, the stretchable laminate of the present invention can express both excellent non-elasticity and excellent elasticity, can achieve both the weight reduction and the extension strength to a larger extent, and can be more stably produced.

When the stretchable laminate of the present invention has stretched portions and non-stretched portions arranged along the CD direction, an area ratio (stretched portions: non-stretched portions) between the stretched portions and the non-stretched portions is preferably from 1:0.5 to 1:3, more preferably from 1:0.5 to 1:2.5, still more preferably from 1:0.5 to 1:2, particularly preferably from 1:0.5 to 1:1.5, most preferably from 1:0.5 to 1:1.2. When the area ratio (stretched portions:non-stretched portions) falls within the range, the stretchable laminate of the present invention can achieve both the weight reduction and the extension strength to a larger extent, and can be more stably produced.

The stretchable laminate of the present invention is subjected to pre-stretching in order that the stretchable laminate may be caused to express excellent elastic performance. The pre-stretching is pre-stretching having the following meaning: the stretchable laminate of the present invention may be stretched again in its final use (e.g., at the time of the production of a diaper and at the time of the use of the diaper).

The pre-stretching is preferably performed after the stretchable laminate of the present invention has been sufficiently solidified in its production process.

The pre-stretching is preferably partial stretching. The pre-stretching may be performed in any appropriate direction, and is preferably stretching in the CD direction.

The stretching ratio of the pre-stretching is preferably 50% or more and less than 1,000%, more preferably 100% or more and less than 900%, still more preferably 300% or more and less than 850%, particularly preferably 500% or more and less than 800%. For example, 100% pre-stretching means that the laminate is stretched by a factor of 2. The stretchable laminate of the present invention can express more excellent elastic performance when pre-stretched at such stretching ratio.

When the stretchable laminate of the present invention has stretched portions and non-stretched portions arranged along the CD direction, the stretched portions and the non-stretched portions are preferably formed by roll stretching in which two uneven rolls each having recessed portions and protruded portions different from each other in diameter are engaged with each other with their recessed portions and protruded portions. The stretchable laminate having stretched portions and non-stretched portions thus formed can achieve both the weight reduction and the extension strength to a larger extent, and can be more stably produced.

Figure 3:
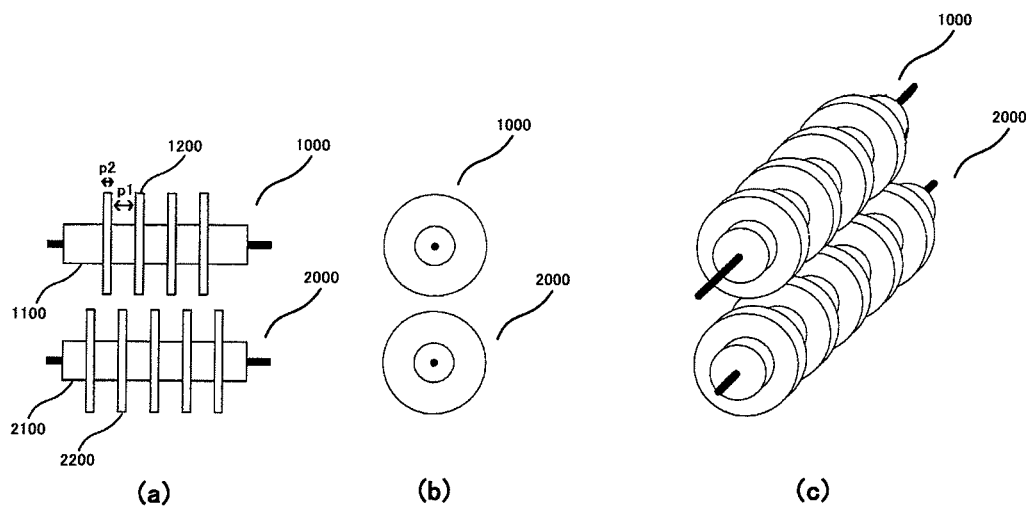
FIG. 3 are each a schematic view of one embodiment of a roll stretching apparatus in a state before a laminate is passed through a space between two uneven rolls to be turned into a stretchable laminate.
Figure 4:
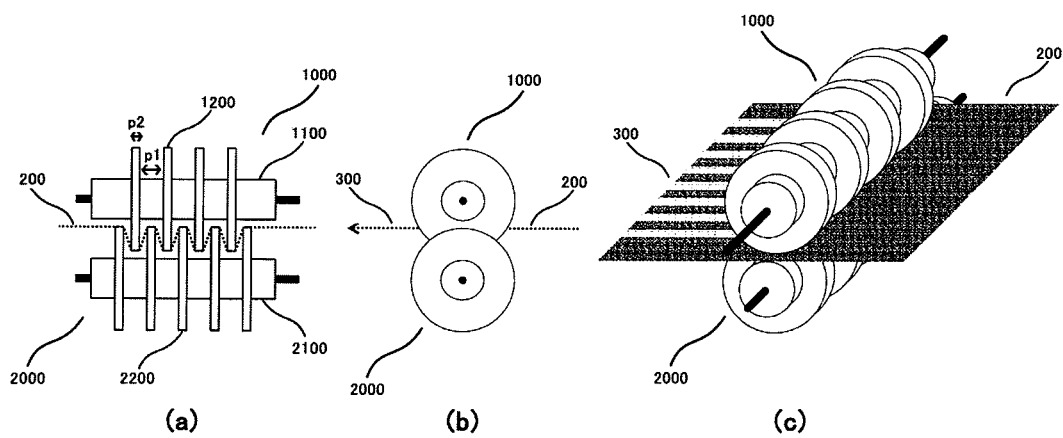
FIG. 4 are each a schematic view of one embodiment of the roll stretching apparatus in a state when the laminate is passed through the space between the two uneven rolls to be turned into a stretchable laminate of the present invention.

FIG. 3 and FIG. 4 are each a schematic view of one embodiment of a roll stretching apparatus in which two uneven rolls each having recessed portions and protruded portions different from each other in diameter are engaged with each other with their recessed portions and protruded portions, the apparatus being capable of being used for forming the stretched portions and the non-stretched portions when the stretchable laminate of the present invention has the stretched portions and the non-stretched portions alternately arranged along the CD direction, and FIG. 3($a$) or 4($a$), FIG. 3($b$) or 4($b$), and FIG. 3($c$) or 4($c$) are a schematic front view, a schematic side view, and a schematic perspective view, respectively.

FIG. 3 are each a schematic view of one embodiment of the roll stretching apparatus in a state before a laminate is passed through a space between the two uneven rolls to be turned into a stretchable laminate. In each of FIG. 3, a roll 1000 and a roll 2000 are arranged so as to face each other. The roll 1000 has a small-diameter roll portion 1100 and large-diameter roll portions 1200. The large-diameter roll portions 1200 serve as the protruded portions, and a space between the two adjacent large-diameter roll portions 1200 serve as the recessed portion. The roll 2000 has a small-diameter roll portion 2100 and large-diameter roll portions 2200. The large-diameter roll portions 2200 serve as the protruded portions, and a space between the two adjacent large-diameter roll portions 2200 serve as the recessed portion. As illustrated in FIG. 3($a$), the roll 1000 and the roll 2000 are arranged so that the protruded portions of the roll 1000 may engage with the recessed portions of the roll 2000 (arranged so that the recessed portions of the roll 1000 may engage with the protruded portions of the roll 2000).

FIG. 4 are each a schematic view of one embodiment of the roll stretching apparatus in a state when the laminate is passed through the space between the two uneven rolls to be turned into the stretchable laminate of the present invention. As illustrated in each of FIG. 4, in order that the stretchable laminate of the present invention may be obtained, a laminate 200 having an elongate shape and including an olefin-based resin layer on at least one side of an elastomer layer is passed through the space between the two uneven rolls (the roll 1000 and the roll 2000), and at the same time, the two uneven rolls (the roll 1000 and the roll 2000) are arranged so that their recessed portions and protruded portions may engage with each other. Thus, as illustrated in FIG. 4(a), a protruded portion (large-diameter roll portion 1200) of the roll 1000 engages with a recessed portion (space between the two adjacent large-diameter roll portions 2200) of the roll 2000, and hence the laminate 200 is stretched at the site of the recessed portion (space between the two adjacent large-diameter roll portions 2200) of the roll 2000. When the laminate 200 having an elongate shape passes through the space between the two uneven rolls (the roll 1000 and the roll 2000) as described above, a stretchable laminate 300 having stretched portions and non-stretched portions alternately arranged along its CD direction as illustrated in FIG. 4(c) is obtained.

The pitch width (p1 of FIG. 3(a)) of each of the recessed portions is preferably larger than the pitch width (p2 of FIG. 3(a)) of each of the protruded portions. The stretchable laminate having stretched portions and non-stretched portions formed so as to be in such state can achieve both the weight reduction and the extension strength to a larger extent, and can be more stably produced.

The pitch width of each of the recessed portions is preferably from 0.5 mm to 5 mm, more preferably from 1 mm to 4 mm, still more preferably from 1.2 mm to 3 mm, particularly preferably from 1.5 mm to 2.5 mm. When the pitch width of each of the recessed portions falls within the range, the stretchable laminate of the present invention can achieve both the weight reduction and the extension strength to a larger extent, and can be more stably produced.

The pitch width of each of the protruded portions is preferably from 0.1 mm to 3 mm, more preferably from 0.2 mm to 2.5 mm, still more preferably from 0.3 mm to 2 mm, particularly preferably from 0.5 mm to 1.5 mm. When the pitch width of each of the protruded portions falls within the range, the stretchable laminate of the present invention can achieve both the weight reduction and the extension strength to a larger extent, and can be more stably produced.

The pre-extension is preferably performed at a temperature less than the melting point of one of the elastomer layer and the olefin-based resin layer. The stretchable laminate of the present invention can express more excellent elastic performance when pre-extended at such temperature.

When the stretchable laminate of the present invention is preferably pre-extended as described above, the olefin-based resin layer undergoes plastic deformation or is extended beyond the brittle fracture point of the olefin-based resin layer, and hence the laminate can express excellent elastic performance. That is, it is preferred that the stretchable laminate of the present invention before the pre-extension hardly express its elasticity by virtue of the presence of the olefin-based resin layer and hence show satisfactory handleability, and meanwhile, the laminate after the pre-extension can express excellent elastic performance.

<<Elastomer Layer>>

Any appropriate number may be adopted as the number of the elastomer layers. The number of such elastomer layers is preferably from 1 to 5, more preferably from 1 to 3, still more preferably 1 or 2, particularly preferably 1.

When the number of the elastomer layers is two or more, all of the respective layers may be layers of the same kind, or at least two of the layers may be layers of different kinds.

The elastomer layer may contain any appropriate resin to the extent that the effects of the present invention are not impaired. Examples of such resin include an olefin-based elastomer and a styrene-based elastomer. The elastomer layer preferably contains the olefin-based elastomer. When the elastomer layer contains the olefin-based elastomer, the effects of the present invention can be expressed to a larger extent, and the stretchable laminate of the present invention can be more excellent in oil resistance.

The olefin-based elastomer may be only one kind of elastomer, or may be a blend of two or more kinds of elastomers.

When the elastomer layer contains the olefin-based elastomer, heat stability is improved and hence, for example, heat decomposition in the production of the stretchable laminate of the present invention can be suppressed. In addition, when the elastomer layer contains the olefin-based elastomer, storage stability is improved and hence the fluctuation of values for physical properties during the storage of the stretchable laminate of the present invention can be suppressed.

In addition, when the elastomer layer contains the olefin-based elastomer, steps in the production of the elastomer layer can be simplified, and hence processing cost can be suppressed. This is because of the following reason: when the olefin-based elastomer is adopted, extrusion molding can be performed by using fewer kinds of resins in the production of the elastomer layer, and hence the need for the production of a master batch can be eliminated.

The content of the olefin-based elastomer in the elastomer layer is preferably from 50 wt % to 100 wt %, more preferably from 70 wt % to 100 wt %, still more preferably from 80 wt % to 100 wt %, particularly preferably from 90 wt % to 100 wt %, most preferably from 95 wt % to 100 wt % because the effects of the present invention are expressed to a larger extent. When the content of the olefin-based elastomer in the elastomer layer is set within the range, the effects of the present invention can be expressed to a larger extent, and the stretchable laminate of the present invention can be more excellent in oil resistance.

Examples of the olefin-based elastomer include an olefin block copolymer, an olefin random copolymer, an ethylene copolymer, a propylene copolymer, an ethylene olefin block copolymer, a propylene olefin block copolymer, an ethylene olefin random copolymer, a propylene olefin random copolymer, an ethylene propylene random copolymer, an ethylene (1-butene) random copolymer, an ethylene (1-pentene) olefin block copolymer, an ethylene (1-hexene) random copolymer, an ethylene (1-heptene) olefin block copolymer, an ethylene (1-octene) olefin block copolymer, an ethylene (1-nonene) olefin block copolymer, an ethylene (1-decene) olefin block copolymer, a propylene ethylene olefin block copolymer, an ethylene (α-olefin) copolymer, an ethylene (α-olefin) random copolymer, an ethylene (α-olefin) block copolymer, and combinations thereof.

The olefin-based elastomer has a density of preferably from 0.890 g/cm$^3$ to 0.830 g/cm$^3$, more preferably from 0.888 g/cm$^3$ to 0.835 g/cm$^3$, still more preferably from 0.886 g/cm$^3$ to 0.835 g/cm$^3$, particularly preferably from 0.885 g/cm$^3$ to 0.840 g/cm$^3$, most preferably from 0.885 g/cm$^3$ to 0.845 g/cm$^3$. When the olefin-based elastomer whose density falls within the range is incorporated into the elastomer layer, the effects of the present invention can be expressed to a larger extent, and the stretchable laminate of the present invention can be more excellent in oil resistance.

The olefin-based elastomer has a MFR at 230° C. and 2.16 kgf of preferably from 1.0 g/10 min to 25.0 g/10 min, more preferably from 2.0 g/10 min to 23.0 g/10 min, still more preferably from 2.0 g/10 min to 21.0 g/10 min, particularly preferably from 2.0 g/10 min to 20.0 g/10 min, most preferably from 2.0 g/10 min to 19.0 g/10 min. When the olefin-based elastomer whose MFR falls within the range is incorporated into the elastomer layer, the effects of the present invention can be expressed to a larger extent, and the stretchable laminate of the present invention can be more excellent in oil resistance.

The olefin-based elastomer is specifically preferably an α-olefin-based elastomer. That is, the α-olefin-based elastomer is a copolymer of two or more kinds of α-olefins and has elastomer characteristics. Of such α-olefin-based elastomers, any one selected from an ethylene-based elastomer, a propylene-based elastomer, and a 1-butene-based elastomer is more preferred. When such α-olefin-based elastomer is adopted as the olefin-based elastomer, the effects of the present invention can be expressed to a larger extent, and the stretchable laminate of the present invention can be more excellent in oil resistance.

Of the α-olefin-based elastomers, an ethylene-based elastomer or a propylene-based elastomer is particularly preferred. When the ethylene-based elastomer or the propylene-based elastomer is adopted as the olefin-based elastomer, the stretchable laminate of the present invention can express the effects of the present invention to a larger extent, and the stretchable laminate of the present invention can be more excellent in oil resistance.

The α-olefin-based elastomer is also available as a commercial product. Examples of such commercial product include some products in the "Tafmer" (trademark) series (e.g., Tafmer PN-3560) manufactured by Mitsui Chemicals, Inc., and some products in the "Vistamaxx" (trademark) series (e.g., Vistamaxx 6202 and Vistamaxx 7010) manufactured by Exxon Mobil Corporation.

The α-olefin-based elastomer is preferably produced by using a metallocene catalyst. When the α-olefin-based elastomer produced by using the metallocene catalyst is adopted, the stretchable laminate of the present invention can express the effects of the present invention to a larger extent, and the stretchable laminate of the present invention can be more excellent in oil resistance.

The elastomer layer may contain any appropriate other component to the extent that the effects of the present invention are not impaired. Examples of such other component include any other polymer, a tackifier, a plasticizer, an antidegradant, a pigment, a dye, an antioxidant, an antistatic agent, a lubricant, a foaming agent, a heat stabilizer, a light stabilizer, an inorganic filler, and an organic filler. Those components may be used alone or in combination thereof. The content of the other component in the elastomer layer is preferably 10 wt % or less, more preferably 7 wt % or less, still more preferably 5 wt % or less, particularly preferably 2 wt % or less, most preferably 1 wt % or less.

The thickness of the elastomer layer is preferably from 8 µm to 450 µm, more preferably from 8 µm to 220 µm, still more preferably from 8 µm to 180 µm, particularly preferably from 8 µm to 90 µm, most preferably from 8 µm to 67 µm. When the thickness of the elastomer layer is set within such range, a stretchable laminate having more excellent fittability can be provided. In addition, when the thickness of the elastomer layer is set within such range, the stretchable laminate of the present invention can be reduced in weight, and hence can be easily used as a material to be used in an article such as a sanitary article, for example, a diaper or a mask.

<<Olefin-Based Resin Layer>>

Any appropriate number may be adopted as the number of the olefin-based resin layers. The number of such olefin-based resin layers is preferably from 1 to 5, more preferably from 1 to 3, still more preferably 1 or 2, particularly preferably 2 (e.g., one olefin-based resin layer is arranged on each of both sides of the elastomer layer).

When the number of the olefin-based resin layers is two or more, all of the respective layers may be layers of the same kind, or at least two of the layers may be layers of different kinds.

The olefin-based resin layer may contain any appropriate resin to the extent that the effects of the present invention are not impaired. The olefin-based resin layer preferably contains a non-elastomeric olefin-based resin. The non-elastomeric olefin-based resin means an olefin-based resin that is not an elastomeric olefin-based resin. When the olefin-based resin layer contains the non-elastomeric olefin-based resin, the effects of the present invention can be expressed to a larger extent, and the stretchable laminate of the present invention can be more excellent in oil resistance, and can also be more excellent in blocking resistance.

The non-elastomeric olefin-based resin may be only one kind of resin, or may be a blend or copolymer of two or more kinds of resins.

The content of the non-elastomeric olefin-based resin in the olefin-based resin layer is preferably from 50 wt % to 100 wt %, more preferably from 70 wt % to 100 wt %, still more preferably from 80 wt % to 100 wt %, particularly preferably from 90 wt % to 100 wt %, most preferably from 95 wt % to 100 wt % because the effects of the present invention are expressed to a larger extent. When the content of the non-elastomeric olefin-based resin in the olefin-based resin layer is set within the range, the effects of the present invention can be expressed to a larger extent, and the stretchable laminate of the present invention can be more excellent in oil resistance, and can also be more excellent in blocking resistance.

Examples of the non-elastomeric olefin-based resin include an α-olefin homopolymer, a copolymer of two or more kinds of α-olefins, block polypropylene, random polypropylene, and a copolymer of one or two or more kinds of α-olefins and any other vinyl monomer. A copolymerization form in any such copolymer is, for example, a block form or a random form.

Examples of the α-olefin include α-olefins each having 2 to 12 carbon atoms. Examples of such α-olefin include ethylene, propylene, 1-butene, and 4-methyl-1-pentene.

Examples of the α-olefin homopolymer include polyethylene (PE), homopolypropylene (PP), poly(1-butene), and poly(4-methyl-1-pentene).

Examples of the polyethylene (PE) include low-density polyethylene (LDPE), linear low-density polyethylene (LLDPE), medium-density polyethylene (MDPE), and high-density polyethylene (HDPE).

The structure of the homopolypropylene (PP) may be any one of isotactic, atactic, and syndiotactic structures.

The non-elastomeric olefin-based resin preferably contains the α-olefin homopolymer, more preferably contains at least one kind selected from polyethylene (PE) and homopolypropylene (PP), and still more preferably contains at least one kind selected from high-density polyethylene (HDPE) and homopolypropylene (PP) because the effects of the present invention can be expressed to a larger extent. When the non-elastomeric olefin-based resin contains at least one kind selected from the high-density polyethylene (HDPE) and the homopolypropylene (PP), a stretchable laminate even more excellent in oil resistance can be provided. The content of the α-olefin homopolymer in the non-elastomeric olefin-based resin is preferably from 50 wt % to 100 wt %, more preferably from 70 wt % to 100 wt %, still more preferably from 80 wt % to 100 wt %, still further more preferably from 90 wt % to 100 wt %, particularly preferably from 95 wt % to 100 wt %, most preferably substantially 100 wt % because the effects of the present invention can be expressed to a larger extent.

Examples of the copolymer of two or more kinds of α-olefins include an ethylene/propylene copolymer, an ethylene/1-butene copolymer, an ethylene/propylene/1-butene copolymer, a copolymer of ethylene/α-olefin having 5 to 12 carbon atoms, and a copolymer of propylene/α-olefin having 5 to 12 carbon atoms.

Examples of the copolymer of one or two or more kinds of α-olefins and any other vinyl monomer include an ethylene/vinyl acetate copolymer, an ethylene/acrylic acid alkyl ester copolymer, an ethylene/methacrylic acid alkyl ester copolymer, and an ethylene-non-conjugated diene copolymer.

A commercial product may be used as the non-elastomeric olefin-based resin.

The olefin-based resin layer may contain any appropriate other component to the extent that the effects of the present invention are not impaired. Examples of such other component include a releasing agent, a UV absorber, a heat stabilizer, a filler, a lubricant, a colorant (e.g., a dye), an antioxidant, an anti-build up agent, an antiblocking agent, a foaming agent, and polyethyleneimine. Those components may be used alone or in combination thereof. The content of the other component in the olefin-based resin layer is preferably 10 wt % or less, more preferably 7 wt % or less, still more preferably 5 wt % or less, particularly preferably 2 wt % or less, most preferably 1 wt % or less.

Examples of the releasing agent include a fatty acid amide-based releasing agent, a silicone-based releasing agent, a fluorine-based releasing agent, and a long-chain alkyl-based releasing agent. Of those, a fatty acid amide-based releasing agent is preferred from the viewpoint that a peeling layer more excellent in balance between peelability and resistance against contamination due to bleedout can be formed, and a saturated fatty acid bisamide is more preferred. Any appropriate content may be adopted as the content of the releasing agent. Typically, the content is preferably from 0.01 wt % to 5 wt % with respect to a resin component (preferably the non-elastomeric olefin-based resin) in the olefin-based resin layer.

Examples of the UV absorber include a benzotriazole-based compound, a benzophenone-based compound, and a benzoate-based compound. Any appropriate content may be adopted as the content of the UV absorber as long as the UV absorber does not bleed out at the time of the forming. Typically, the content is preferably from 0.01 wt % to 5 wt % with respect to the resin component (preferably the non-elastomeric olefin-based resin) in the olefin-based resin layer.

Examples of the heat stabilizer include a hindered amine-based compound, a phosphorus-based compound, and a cyanoacrylate-based compound. Any appropriate content may be adopted as the content of the heat stabilizer as long as the heat stabilizer does not bleed out at the time of the forming. Typically, the content is preferably from 0.01 wt % to 5 wt % with respect to the resin component (preferably the non-elastomeric olefin-based resin) in the olefin-based resin layer.

Examples of the filler include inorganic fillers, such as talc, titanium oxide, calcium oxide, magnesium oxide, zinc oxide, calcium carbonate, silica, clay, mica, barium sulfate, whisker, and magnesium hydroxide. The average particle diameter of the filler is preferably from 0.1 μm to 20 μm. Any appropriate content may be adopted as the content of the filler. Typically, the content is preferably from 1 wt % to 200 wt % with respect to the resin component (preferably the non-elastomeric olefin-based resin) in the olefin-based resin layer.

The thickness of the olefin-based resin layer is preferably from 2 μm to 50 μm, more preferably from 2 μm to 30 μm, still more preferably from 2 μm to 20 μm, particularly preferably from 2 μm to 10 μm, most preferably from 2 μm to 8 μm. When the thickness of the olefin-based resin layer is set within such range, the stretchable laminate of the present invention can be reduced in weight, and can be easily used as a material to be used in an article such as a sanitary article, for example, a diaper or a mask.

<<Production of Stretchable Laminate>>

Any appropriate method may be adopted as a method of producing the stretchable laminate of the present invention to the extent that the effects of the present invention are not impaired as long as such a construction that the olefin-based resin layer is arranged on at least one side of the elastomer layer can be built by the method.

The method of producing the stretchable laminate of the present invention is typically, for example, a production method involving molding a laminate with a multilayer extrusion T-die molding machine. For example, when a stretchable laminate formed of a laminated construction "olefin-based resin layer/elastomer layer/olefin-based resin layer" is produced, a molding material for the olefin-based resin layer, a molding material for the elastomer layer, and a molding material for the olefin-based resin layer are co-extruded from a T-die by using a three-layer extrusion T-die molding machine to be integrated, and the integrated material is preferably subjected to such pre-stretching as described in the foregoing (more preferably such partial stretching as described in the foregoing, still more preferably such partial stretching as described with reference to FIG. 3(a), FIG. 3(b), FIG. 3(c), FIG. 4(a), FIG. 4(b), and FIG. 4(c)), and is then wound in a roll shape. Thus, a rolled body of the stretchable laminate can be produced. In addition to the T-die method involving using the T-die, an inflation method or the like may also be adopted.

<<Application of Stretchable Laminate of the Present Invention>>

The stretchable laminate of the present invention can be used in any appropriate article in which the effects of the present invention can be effectively utilized. That is, the article of the present invention includes the stretchable laminate of the present invention. A typical example of such article is a sanitary article. Examples of such sanitary article include a diaper (in particular, such a diaper that the stretchable laminate of the present invention is used as a stretchable material in an ear portion or a stretchable material in the opening portion of waist surroundings or leg surroundings (a waist band or a gather)), a supporter, and a mask.

EXAMPLES

The present invention is hereinafter specifically described by way of Examples. However, the present invention is by no means limited to these Examples. Test and evaluation methods in Examples and the like are as described below. In addition, "part (s)" means "part(s) by weight" and "%" means "wt %" unless otherwise stated.

<10% Extension Strength in MD Direction>

A stretchable laminate or a laminate obtained in any one of Examples and Comparative Examples was cut into a size of 30 mm in its widthwise direction, and was set in a tension testing machine (manufactured by Shimadzu Corporation: AG-20kNG) at a distance between chucks of 40 mm in its lengthwise direction, followed by the measurement of its tensile strength at the time of its extension by up to 10% at a tension speed of 300 mm/min.

<Basis Weight>

A stretchable laminate or a laminate obtained in any one of Examples and Comparative Examples was cut into a test piece measuring 100 mm in its widthwise direction by 200 mm in its lengthwise direction, and the weight of the test piece was measured with an electronic balance. The measurement was repeated three times, and the basis weight (weight per square meter area) of the test piece was calculated from the average of the weights.

<Evaluation of Blocking Property>

A rolled body of a stretchable laminate or a laminate obtained in any one of Examples and Comparative Examples was cut into a size of 30 mm in its widthwise direction, and was stored in a state at 23° C.×50 RH % for 24 hours. After that, the resultant was rewound at a rewinding speed of 300 mm/min. A case in which the stretchable laminate or the laminate ruptured at the time of the rewinding was evaluated as x, a case in which the stretchable laminate or the laminate did not rupture at the time of the rewinding was evaluated as ○, and a case in which the stretchable laminate or the laminate did not rupture at the time of the rewinding, and no change in rewinding feeling was observed after the storage as compared to the rewinding feeling before the storage was evaluated as ⊚.

<Evaluation of Dropping Oil Resistance>

A stretchable laminate or a laminate obtained in any one of Examples and Comparative Examples was cut into a size measuring 50 mm in its lengthwise direction by 10 mm in its widthwise direction, and was bonded and fixed onto a glass plate in a state of being extended by 100% in the lengthwise direction. 0.5 mL of a baby oil (manufactured by Pigeon Corporation, Baby Oil Q, main component: caprylic/capric triglyceride) was dropped onto the surface of the extended stretchable laminate or laminate, and an evaluation was performed on the basis of the following criteria.

x: 60 Minutes after the dropping, a hole or a crack due to dissolution by the baby oil occurs in the stretchable laminate or the laminate to rupture the stretchable laminate or the laminate.

Δ: 60 Minutes after the dropping, a hole or a crack due to dissolution by the baby oil occurs in the stretchable laminate or the laminate, but the stretchable laminate or the laminate does not rupture.

○: 60 Minutes after the dropping, a hole or a crack due to dissolution by the baby oil is not formed in the stretchable laminate or the laminate.

In the present invention, a "baby oil" using caprylic/capric triglyceride as a main component, such as "Baby Oil P" available from Pigeon Corporation, can be used as the "baby oil" to be used in the dropping oil resistance test in addition to the "Baby Oil Q".

<Elasticity Test>

A stretchable laminate or a laminate obtained in any one of Examples and Comparative Examples was cut into a size of 30 mm in its widthwise direction, and was set in a tension testing machine (manufactured by Shimadzu Corporation: AG-20kNG) at a distance between chucks of 40 mm in its lengthwise direction. The resultant was extended by 100% at a tension speed of 300 mm/min. After having been extended by 100%, the laminate was fixed in an extended state and held at room temperature for 10 minutes. After a lapse of 10 minutes, the laminate was released from the extended state, and the initial distance between the chucks, i.e., 40 mm (A) and the length of the film after the test, i.e., (40+α) mm (B) were measured. After that, a fluctuation ratio was calculated from the expression "[{(B)−(A)}/(A)]×100." A laminate whose fluctuation ratio was more than 20% was evaluated as x, and a laminate whose fluctuation ratio was 20% or less was evaluated as ○.

<Molding Conditions>

In each of Examples and Comparative Examples, a stretchable laminate or a laminate was molded with an extrusion T-die molding machine including three layers in three types (A layer/B layer/C layer). The molding was performed under the following extrusion temperature conditions.

A layer: 200° C.
B layer: 200° C.
C layer: 200° C.
Die temperature: 200° C.

Molding materials were subjected to co-extrusion molding from a T-die to be integrated. The resultant stretchable laminate or laminate was sufficiently solidified, and was then wound in a roll shape. Thus, a rolled body was obtained.

In the case of partial stretching, two uneven rolls in each of which the pitch width of each of protruded portions was 1 mm and the pitch width of each of recessed portions (interval between a protruded portion and an adjacent protruded portion) was 2 mm were vertically superimposed on each other by 3.5 mm, and the stretchable laminate or the laminate fed from the rolled body was passed through a space between the rolls at a speed of 20 m/min to be stretched by 700%.

In the case of overall stretching, the edges of the stretchable laminate or the laminate fed from the rolled body were grasped with tenter clips, and the stretchable laminate or the laminate was extended by 400% in its widthwise direction.

Example 1

HDPE (manufactured by Tosoh Corporation, product name: Nipolon Hard 1000) serving as a non-elastomeric olefin-based resin was loaded into the A layer of an extruder, EPR (manufactured by Exxon Mobil Corporation, product name: Vistamaxx 6202) serving as an olefin-based elastomer was loaded into the B layer of the extruder, and HDPE (manufactured by Tosoh Corporation, product name: Nipolon Hard 1000) serving as a non-elastomeric olefin-based resin was loaded into the C layer of the extruder, followed by the extrusion of a laminate having a total thickness of 40 μm in which the thicknesses of the A layer, the B layer, and the C layer were 4 μm, 32 μm, and 4 μm, respectively. The resultant laminate was partially stretched to provide a stretchable laminate (1).

The results are shown in Table 1.

Example 2

A stretchable laminate (2) was obtained in the same manner as in Example 1 except that HDPE (manufactured by Basell, product name: 52518) was used as a non-elastomeric olefin-based resin.

The results are shown in Table 1.

Example 3

A stretchable laminate (3) was obtained in the same manner as in Example 1 except that the thicknesses of the A layer, the B layer, and the C layer were set to 5.5 μm, 44 μm, and 5.5 μm, respectively, i.e., the total thickness was set to 55 μm.

The results are shown in Table 1.

Example 4

A stretchable laminate (4) was obtained in the same manner as in Example 1 except that EPR (manufactured by Exxon Mobil Corporation, product name: Vistamaxx 7010) was used as an olefin-based elastomer.

The results are shown in Table 1.

Example 5

A stretchable laminate (5) was obtained in the same manner as in Example 1 except that instead of the olefin-based elastomer, SIS (manufactured by Zeon Corporation, product name: Quintac 3390) was used as a styrene-based elastomer.

The results are shown in Table 1.

Example 6

A stretchable laminate (6) was obtained in the same manner as in Example 1 except that instead of the olefin-based elastomer, SBS (manufactured by Kraton Corporation, product name: Kraton D1191) was used as a styrene-based elastomer.

The results are shown in Table 1.

Comparative Example 1

A stretchable laminate (C1) was obtained in the same manner as in Example 1 except that the overall stretching was performed instead of the partial stretching.

The results are shown in Table 1.

Comparative Example 2

A stretchable laminate (C2) was obtained in the same manner as in Example 3 except that the overall stretching was performed instead of the partial stretching.

The results are shown in Table 1.

TABLE 1

| | | Examples | | | | | |
|---|---|---|---|---|---|---|---|
| | | 1 | 2 | 3 | 4 | 5 | 6 |
| A layer resin | | Nipolon Hard 1000 | 52518 | Nipolon Hard 1000 | Nipolon Hard 1000 | Nipolon Hard 1000 | Nipolon Hard 1000 |
| B layer resin | | Vistamaxx 6202 | Vistamaxx 6202 | Vistamaxx 6202 | Vistamaxx 7010 | Quintac 3390 | Kraton D1191 |
| C layer resin | | Nipolon Hard 1000 | 52518 | Nipolon Hard 1000 | Nipolon Hard 1000 | Nipolon Hard 1000 | Nipolon Hard 1000 |
| A/B/C thickness | μm | 4/32/4 | 4/32/4 | 5.5/44/5.5 | 4/32/4 | 4/32/4 | 4/32/4 |
| Total thickness of laminate | μm | 40 | 40 | 55 | 40 | 40 | 40 |
| Basis weight of laminate | gsm | 34.7 | 34.5 | 47.6 | 34.6 | 35.5 | 34.9 |
| Stretching mode | | Partial stretching | Partial stretching | Partial stretching | Partial stretching | Partial stretching | Partial stretching |
| Basis weight X after stretching | gsm | 31.8 | 31.1 | 42.8 | 32.0 | 31.3 | 31.4 |
| 10% extension strength Y in MD direction | N/30 mm | 5.5 | 5.7 | 7.4 | 5.2 | 6.0 | 5.7 |
| Y/X | N/30 mm · gsm | 0.17 | 0.18 | 0.17 | 0.16 | 0.19 | 0.18 |
| Blocking property | | ◎ | ◎ | ◎ | ◎ | ◎ | ◎ |
| Dropping oil resistance | | ○ | ○ | ○ | ○ | Δ | Δ |
| Elasticity | | ○ | ○ | ○ | ○ | ○ | ○ |

| | | Comparative Examples | |
|---|---|---|---|
| | | 1 | 2 |
| A layer resin | | Nipolon Hard 1000 | Nipolon Hard 1000 |
| B layer resin | | Vistamaxx 6202 | Vistamaxx 6202 |
| C layer resin | | Nipolon Hard 1000 | Nipolon Hard 1000 |
| A/B/C thickness | μm | 4/32/4 | 5.5/44/5.5 |
| Total thickness of laminate | μm | 40 | 55 |
| Basis weight of laminate | gsm | 34.7 | 47.6 |

TABLE 1-continued

| Stretching mode | | Overall stretching | Overall stretching |
|---|---|---|---|
| Basis weight X after stretching | gsm | 25.1 | 31.4 |
| 10% extension strength Y in MD direction | N/30 mm | 2.6 | 4.1 |
| Y/X | N/30 mm · gsm | 0.10 | 0.13 |
| Blocking property | | ○ | ○ |
| Dropping oil resistance | | ○ | ○ |
| Elasticity | | ○ | ○ |

INDUSTRIAL APPLICABILITY

The stretchable laminate of the present invention can be used in any appropriate article in which the effects of the present invention can be effectively utilized. That is, the article of the present invention includes the stretchable laminate of the present invention. A typical example of such article is a sanitary article. Examples of such sanitary article include a diaper (in particular, such a diaper that the stretchable laminate of the present invention is used as a stretchable material in an ear portion or a stretchable material in the opening portion of waist surroundings or leg surroundings (a waist band or a gather)), a supporter, and a mask.

REFERENCE SIGNS LIST

10 elastomer layer
20a olefin-based resin layer
20b olefin-based resin layer
30 stretched portion
40 non-stretched portion
100 stretchable laminate
200 laminate
300 stretchable laminate
1000 roll
1100 small-diameter roll portion
1200 large-diameter roll portion
2000 roll
2100 small-diameter roll portion
2200 large-diameter roll portion

The invention claimed is:

1. A stretchable laminate having an elongate shape, the stretchable laminate comprising:
   an elastomer layer that contains an olefin-based elastomer, wherein the content of the olefin-based elastomer in the elastomer layer is 80 wt % to 100 wt %, the olefin-based elastomer having a melt flow rate (MFR) at 230° C. and 2.16 kgf of from 1.0 g/10 min to 25.0 g/10 min, and the olefin-based elastomer having a density of from 0.830 g/cm³ to 0.890 g/cm³; and
   an olefin-based resin layer arranged on at least one side of the elastomer layer,
   a longitudinal direction of the stretchable laminate is defined as an MD direction and a direction perpendicular to the longitudinal direction is defined as a CD direction, a ratio [10% extension strength in MD direction (N/30 mm)]/[basis weight (gsm)] of the stretchable laminate is 0.14 (N/30 mm·gsm) or more,
   the stretchable laminate having stretched portions and non-stretched portions arranged along the CD direction, and
   an area ratio (stretched portions:non-stretched portions) between the stretched portions and the non-stretched portions is from 1:0.5 to 1:3.

2. The stretchable laminate according to claim 1, wherein the ratio [10% extension strength in MD direction (N/30 mm)]/[basis weight (gsm)] is 0.15 (N/30 mm·gsm) or more.

3. The stretchable laminate according to claim 2, wherein the stretched portions and the non-stretched portions are alternately arranged along the CD direction.

4. The stretchable laminate according to claim 2, wherein the stretched portions and the non-stretched portions are formed by roll stretching in which two uneven rolls each having recessed portions and protruded portions different from each other in diameter are engaged with each other with the recessed portions and the protruded portions thereof.

5. The stretchable laminate according to claim 4, wherein a pitch width of each of the recessed portions is larger than a pitch width of each of the protruded portions.

6. The stretchable laminate according to claim 4, wherein a pitch width of each of the recessed portions is from 0.5 mm to 5 mm, and a pitch width of each of the protruded portions is from 0.1 mm to 3 mm.

7. The stretchable laminate according to claim 1, wherein when the stretchable laminate is bonded and fixed onto a glass plate in a state of being extended by 100%, and 0.5 mL of a baby oil (manufactured by Pigeon Corporation, Baby Oil, main component: caprylic/capric triglyceride) is dropped onto a surface of the stretchable laminate, the stretchable laminate is free of a hole 60 minutes after the dropping.

8. The stretchable laminate according to claim 1, wherein the olefin-based resin layer is arranged on each of both sides of the elastomer layer.

9. The stretchable laminate according to claim 8, wherein the olefin-based resin layer contains a non-elastomeric olefin-based resin.

10. The stretchable laminate according to claim 9, wherein a content of the non-elastomeric olefin-based resin in the olefin-based resin layer is from 95 wt % to 100 wt %.

11. The stretchable laminate according to claim 9, wherein the non-elastomeric olefin-based resin contains high-density polyethylene.

12. The stretchable laminate according to claim 8, wherein the olefin-based elastomer comprises an α-olefin-based elastomer.

13. The stretchable laminate according to claim 1, wherein the olefin-based resin layer contains a non-elastomeric olefin-based resin.

14. The stretchable laminate according to claim 13, wherein a content of the non-elastomeric olefin-based resin in the olefin-based resin layer is from 95 wt % to 100 wt %.

15. The stretchable laminate according to claim 13, wherein the non-elastomeric olefin-based resin contains high-density polyethylene.

16. The stretchable laminate according to claim 1, wherein the olefin-based elastomer comprises an α-olefin-based elastomer.

17. The stretchable laminate according to claim 1, wherein the stretched portions and the non-stretched portions are alternately arranged along the CD direction.

18. The stretchable laminate according to claim 1, wherein the stretched portions and the non-stretched portions are formed by roll stretching in which two uneven rolls each having recessed portions and protruded portions different from each other in diameter are engaged with each other with the recessed portions and the protruded portions thereof.

19. The stretchable laminate according to claim 18, wherein a pitch width of each of the recessed portions is larger than a pitch width of each of the protruded portions.

20. The stretchable laminate according to claim 18, wherein a pitch width of each of the recessed portions is from 0.5 mm to 5 mm, and a pitch width of each of the protruded portions is from 0.1 mm to 3 mm.

21. The stretchable laminate according to claim 1, wherein the stretchable laminate is subjected to pre-stretching.

22. The stretchable laminate according to claim 21, wherein the pre-stretching comprises partial stretching.

23. The stretchable laminate according to claim 22, wherein a stretching ratio of the partial stretching is 100% or more and less than 900%.

24. The stretchable laminate according to claim 1, wherein the stretchable laminate is used in a sanitary article.

25. An article, comprising the stretchable laminate of claim 1.

* * * * *